United States Patent [19]

van den Bosch

[11] Patent Number: 4,624,572
[45] Date of Patent: Nov. 25, 1986

[54] NON-INVASIVE REFLECTANCE SPECTROPHOTOMETRIC APPARATUS

[76] Inventor: Francois J. G. van den Bosch, 10209 Eisenhower La., Great Falls, Va. 22066

[21] Appl. No.: 591,831

[22] Filed: Mar. 21, 1984

Related U.S. Application Data

[63] Continuation-in-part of Ser. No. 346,147, Feb. 5, 1982, abandoned.

[51] Int. Cl.⁴ .......................... G01J 3/51; G01N 21/27
[52] U.S. Cl. .................................... 356/418; 250/210; 356/446
[58] Field of Search .................. 356/418, 445–448; 250/210

[56] References Cited

U.S. PATENT DOCUMENTS

| | | | |
|---|---|---|---|
| 2,451,501 | 10/1948 | Liben | 356/445 |
| 3,421,821 | 1/1969 | Alessi | 356/445 X |
| 3,846,027 | 11/1974 | Hyman et al. | 356/418 |
| 4,082,458 | 4/1978 | Fukui et al. | 356/445 X |

FOREIGN PATENT DOCUMENTS

| | | | |
|---|---|---|---|
| 2855578 | 7/1979 | Fed. Rep. of Germany | 356/418 |
| 2414726 | 9/1979 | France | 356/445 |

*Primary Examiner*—Vincent P. McGraw
*Attorney, Agent, or Firm*—Watson, Cole, Grindle and Watson

[57] ABSTRACT

Spectrophotometric apparatus is incorporated in a portable housing with a light source for emitting a wide band of radiation from which monochromatic light is produced and projected onto a specimen outside the housing. A hood is mounted to the housing and includes an aperture through which light is emitted from the light source and reflected from either a specimen or a calibrating material positioned in front of the aperture such that light is reflected from either the specimen or the calibrating material onto a photosensitive detector within the housing. The photosensitive detector is responsive to the monochromatic light reflected from the specimen or the calibrating material to provide output signals representative of the spectrophotometric characteristics thereof. The output of the photosensitive detector is connected to an indicating meter.

9 Claims, 4 Drawing Figures

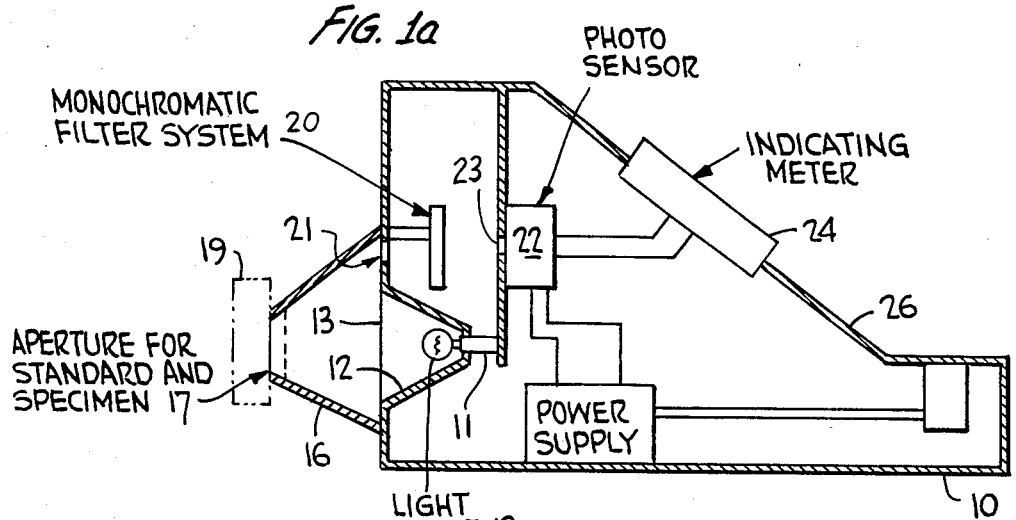
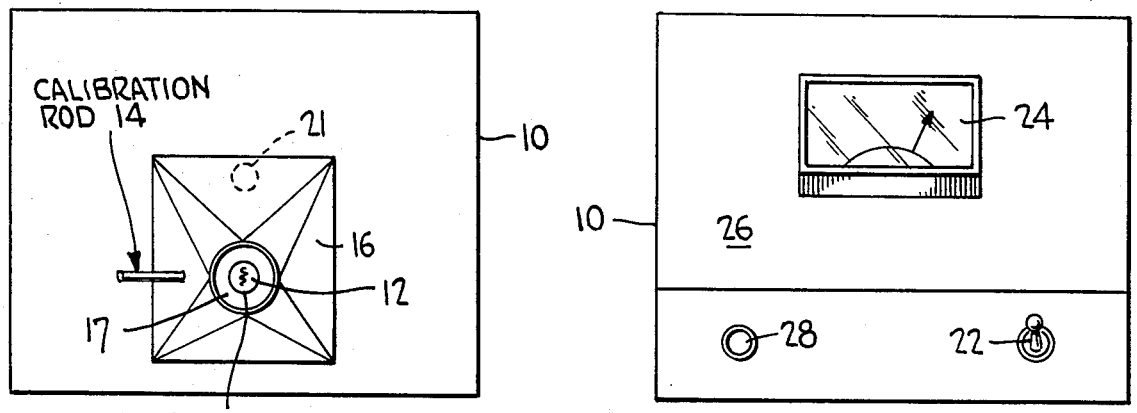
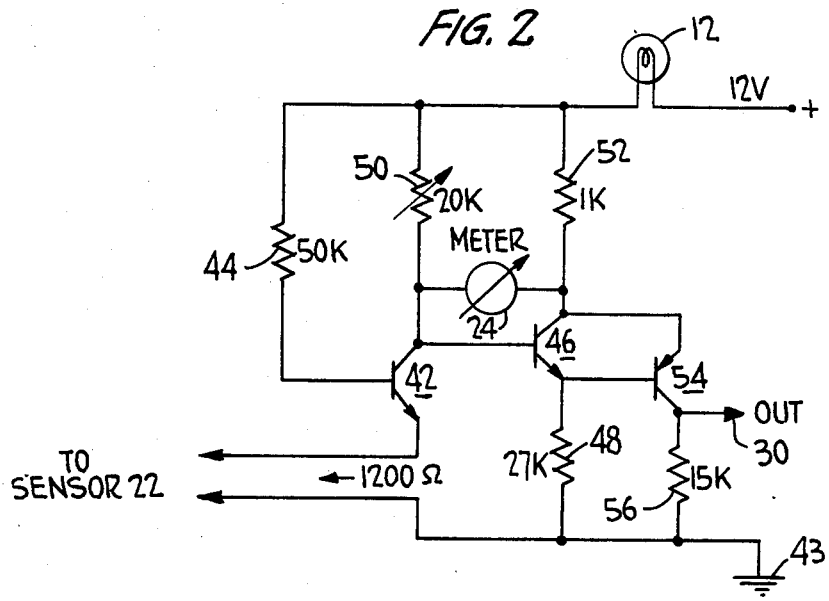

NON-INVASIVE REFLECTANCE SPECTROPHOTOMETRIC APPARATUS

The photoelectric type spectrophotometer or densitometer apparatus of the present invention (hereinafter reference to spectrophotometric apparatus shall be intended to include densitometer, colorimeter or other like apparatus) is a continuation-in-part application of application Ser. No. 346,147, filed Feb. 5, 1982, and now abandoned.

BACKGROUND OF THE INVENTION

The present invention relates to spectrophotometric or densitometer apparatus, and in particular to such apparatus that is portable, easily calibrated, and in which the detection of radiation transmitted from the specimen is enhanced by an electronic bridge sensor.

Spectrophotometric apparatus generally utilize absorption filter devices to select and detect the necessary information to identify the elements or components of a given specimen. Selective absorption is generally achieved with the use of color filters, interference filters, echelon gratings or prisms. In particular, the information obtained from spectrophotometric instruments is produced by passing a light beam, such as is obtained from a monochromatic light source, or simply by means of colored filters, through suitably placed glass transparent recipients in the path of the light beam. The loss of the light by absorption, for example in the specimen or object, is then interpreted in terms of the resultant optical density or induction of the chemical composition of the specimen, or a combination of both optical density and chemical techniques.

Alternatively, the spectrophotometric information or data is obtained by reflecting radiation from a suitable broad band or a narrow band light emitting source, such as a monochromatic light source, or the use of colored filters, interference filters, echelon gratings, or prisms, etc., and collecting the light reflected from a specimen or object by a suitable photosensor, such as a photomultiplier or light sensitive receiver of the solid state type that are well known to those skilled in the art to which the invention is directed. The necessary absorption filters, or narrow band radiation-producing elements are then inserted in the reflected light path between the specimen and the photosensitive device.

The specimen or object may be illuminated with a wide band light source, such as a projection lamp with a color temperature of over 3000 degrees fahrenheit, or a Xenon high pressure arc lamp, with an absorption filter in front of the photoelectric sensor or receiver. Alternatively, a dispersive element such as a grating may be placed in front of the photosensitive device, thereby selecting the precise wavelength at which the absorption occurs.

The advantages of such a technique over the classical photometer, spectrophotometer or colorimeter, is simply that the specimen or object to be examined is irradiated with a higher intensity irradiation than if the light radiation were, for example, monochromatic by the placement or insertion of the filters between the light source and the specimen as opposed to the insertion of the absorption filter between the reflected light rays from the object and the photosensitive element or receiver. However, such techniques have not been completely successful in enhancing and increasing the sensitivity of the photosensitive response of the light radiation detection apparatus, thereby presenting a need for improvement in the latter mentioned apparatus.

SUMMARY OF THE INVENTION

A primary feature of the invention is the enhancement of the spectrophotometric response and versatility of measurement in an electronic measuring apparatus of the portable type. In a preferred embodiment, a bridge measuring circuit incorporates a solid state device, such as a transistor, in one arm with the photosensitive device responsive to the light transmitted from the specimen connected with the solid state device to modify the voltage or current amplification characteristics thereof. For example, in the preferred embodiment described herein, the photosensitive device, such as a light responsive phototransistor, is connected in the emitter of a first transistor to cause a variation in the amplification characteristic thereof. A second solid state device, such as a second transistor, is connected to the first mentioned solid state device to be responsive to the amplified voltage or current characteristic thereof and is connected in a second arm of the bridge. An indicating meter, such as an ammeter or a voltmeter, is connected across the bridge to provide visual indication of the sensed spectrophotometric characteristic. A variable resistance, for calibrating the measuring circuit is connected in a third arm of the bridge opposite the second mentioned solid state device. A voltage dropping resistance is connected in the fourth arm of the bridge opposite the first mentioned solid state device. Another solid state device is connected to the second mentioned solid state device to provide a read out of the sensed spectrophotometric characteristic to a computer and/or recorder apparatus.

The lowered impedance of that bridge circuit with a decrease in the resistance of the photosensitive device resulting from increasing light radiation from the radiation source, causes increased current through the radiation source such that the intensity of radiation therefrom is increased, thereby enhancing and increasing the radiation available for irradiating the specimen. This effect is aided by the amplification factor of the first mentioned solid state device.

Thus, in addition to the advantage obtained by a solid state actuated electronic bridge circuit, which provides increased measurement sensitivity, the invention affords commensurate enhancement of the radiation from the radiation source.

An important feature of the invention is a portable spectrophotometric apparatus which enables information or data identifying a specimen or object to be very rapidly determined with significant precision.

Another significant advantage of the invention is the utilization of an ordinary voltage or ammeter as an indicator which can be easily calibrated by a calibrating substance positioned in front of the portable spectrophotometric apparatus. This enables calibration of the apparatus over a wide bandwidth of radiation.

A further feature of the invention is to provide portable spectrophotometric or densitometer apparatus that is easily calibrated over a narrow wavelength and in which the specimen is irradiated with a white light, or a relative wide band light emission and the light reflected from the sensor apparatus senses light reflected or otherwise transmitted from the specimen within the narrow bandwidth.

Yet a further feature of the invention is to provide portable spectrophotometric or densitometer apparatus in which the measurement of the reflected radiation emanating from the object or specimen is enhanced with a commensurate increase in the detected photosensitive response, thereby enabling improved precision measurements to be made from portable spectrophotometric or densitometer apparatus.

The invention also affords a very simply constructed portable spectrophotometric or densitometer apparatus that is extremely efficient but yet one that enables rapid spectrophotometric analysis to be carried out.

The invention is also characterized in that the portable spectrophotometric or densitometer apparatus can be readily calibrated over a wide bandwidth of radiation.

The invention also provides portable spectrophotometric or densitometer apparatus that is capable of being utilized by relatively unskilled technicians, but yet is sufficiently accurate to afford wide application, especially in the medical field for noninvasive analysis of certain human functions such as surface blood circulation in the extremities of the human body.

The spectrophotometric apparatus is also adaptable to integrated type circuitry. The buffered amplified output of the measuring circuit also makes the inventive apparatus readily usable with computer or recorder apparatus.

BRIEF DESCRIPTION OF THE DRAWINGS

The above objects, advantages and features of the invention are readily apparent to one of ordinary skill in the art of spectrophotometric analysis from the following description of a preferred embodiment representing the best mode of carrying out the invention when taken in conjunction with the following drawings, wherein:

FIG. 1a is a side view of a preferred embodiment of a portable spectrophotometric apparatus in accordance with the invention;

FIGS. 1b and 1c illustrate perspective front and rear views of the spectrophotometric apparatus of FIG. 1a; and FIG. 2 is an electrical schematic of a preferred embodiment of the measuring circuit of the present invention.

DETAILED DESCRIPTION OF THE PREFERRED EMBODIMENT

The embodiment illustrated in FIGS. 1a to 1c represents a practical commercial adaptation of a portable, easily calibratable, and yet sufficiently accurate, spectrophotometric or densitometer apparatus in accordance with the principles of the invention. As illustrated in FIG. 1a, housing 10 includes light source 12 having, for example, wide band output characteristics and which is mounted such that the light radiating therefrom is transmitted through an aperture 13 at the opposite end of the housing.

The light emanating from light source 12 is reflected through hood 16 and passes through aperture 17 at the end thereof and is reflected from a specimen or calibration substance 19 which is positioned over aperture 17. The reflected light is passed through monochromatic filter system 20 through aperture 21 and is then received by photosensor 22 through aperture 23 with the output thereof being indicated by indicating meter 24 mounted on sloping surface 26 of housing 10. Housing 10 may also include a power supply and any other electronics that are necessary to respectively power the detection circuitry and to provide a suitable output, for example, to a computer in addition to a visual indication to the operator. Such electronics may include amplifiers, frequency discriminator networks, and electrical frequency filters.

The portable spectrophotometric or densitometer apparatus of the embodiment in FIG. 1a operates by the operator holding or otherwise positioning specimen 19 in closing relationship to aperture 17 such that substantially only that light reflected or transmitted from the specimen enters aperture 17 and impinges on monochromatic filter system 20. It is not necessary for proper functioning of the spectrophotometric apparatus that the specimen 19 be held or maintained against aperture 17 to prevent extraneous light from entering aperture 17. The spectrophotometric apparatus will operate with the specimen spaced from aperture 17, although with less sensitivity and accuracy. The spectrophotometric or densitometer apparatus of the embodiment herein described can be calibrated from the calibration substance positioned over aperture 17. The apparatus of FIG. 1a, in addition to being portable, provides a simple and inexpensive means for readily determining the spectrophotometric or densitometer characteristics of any number of specimens and is useful in laboratories and medical facilities, such as hospitals in which it may be desirable to quickly determine the content of a blood sample, for example. Such an instrument can be carried by a medical team in an ambulance for use to obtain fast and sufficiently accurate data in emergency situations.

The apparatus illustrated in FIG. 1a can be modified to provide a narrow band of monochromatic light radiation either by use of a narrow band emission light source 12, or by using a wide band light source with means for obtaining narrow band monochromatic emission such as gratings, filter wheels, filter wheels with slits, etc., all known in the art to which the invention is directed. In such circumstances the monochromatic light generating system 20 is unnecessary. Slitted wheels that provide pulsed signal output enable the apparatus of the invention to be operatively connected with computers and digital recording apparatus.

FIG. 1b represents a front view of the spectrophotometric apparatus of FIG. 1a illustrating the mounting of hood 16. In the preferred embodiment of the invention, the size and shape of hood 16 and apertures 17 and 20 are only exemplary. The shapes and sizes of those components can be varied as necessary to maximize the operation of the spectrophotometric apparatus. A calibration rod 14 (not shown in FIG. 1a) can be mounted in operative relationship to hood 16 and aperture 17 such that calibration substances can be attached to rod 14 for calibration of the apparatus in a manner known to the art or as described hereinafter.

FIG. 1c illustrates a back view of the spectrophotometric apparatus of the embodiment shown in FIG. 1a indicating the relative position of indication meber 24 on sloping face 26 of housing 10. On/off switch 22, as well as pilot light 28, may be provided at any convenient location on the exterior of the apparatus.

FIG. 2 illustrates a preferred embodiment of a measuring circuit which receives the output of the photosensor 22 to actuate indicating member 24 or to provide a buffered output signal 30 for input to a computer or recorder. The output from the sensor 22 is input between the emitter of transistor 42 and ground 43. The base of transistor 42 is connected to a +12 volt battery power source through resistance 44 and the collector of transistor 42 is connected to the base of transistor 46; and also to one terminal of indicating meter 24, and to the +12 volt battery power source through variable resistance 50. Variable resistance 50 serves to null or calibrate indicating meter 24 when the sensor 22 detects light radiation from a calibration substance at aperture 17. The emitter of transistor 46 is connected to ground 43 through resistance 48, and the collector of that transistor is connected to the +12 volt battery source through resistance 52. Indicating meter 24 is connected between the collectors of transistors 42 and 46.

The operation of the circuit described above is as follows. It is assumed that the impedance of sensor 22 decreases with increasing light intensity and increases with decreasing light intensity of the received light from a specimen or calibration substance positioned at aperture 17 in FIG. 1a. With a specified calibration substance at aperture 17, variable resistance 50 is adjusted to obtain a null or other specific reference position of indication meter 24. The specimen, the spectrophotometric or density characteristics of which are to be measured, is then placed at aperture 17 and the reading of meter 24 observed by the operator.

Another example of the operation of the apparatus follows.

When a doctor desires to have a quick check of the surface circulation in the hand or foot of a patient, aperture 17 is positioned at the palm or base of the foot, and preferably in abutting relationship thereto to eliminate extraneous light from sensor 22. A reading is obtained to indicate the hue of the color of the palm or base of the foot. A first reading is made to establish a base reference. The indication can be adjusted by variable resistance 50. When, for example, checking the circulation of blood in a patient's legs using the base of the foot for measurement, the first reading should be the base reading. When the leg of the patient is raised subsequently, the spectrophotometric apparatus provides a different indication. Upon lowering the patient's leg the original base reading as described above should be obtained.

Thus, from the above description, it is clearly understood that indicating meter 24 is connected across the respective outputs from the collectors of transistors 42 and 46.

An external buffered output signal can be provided from the emitter of the collector of transistor 54, the emitter-base electrodes of which are connected across the emitter-collector junction of transistor 46. The collector of transistor 46 is connected to ground 43 through resistance 56. The output from the collector of transistor 54 varies in accordance with the emitter-collector voltage of transistor 46 which, in turn, is a function of the impedance of the photosensor in the emitter of transistor 42. That signal output can be utilized as an input to a computer or recorder. For optimum results the forward current characteristics of transistors 42 and 46 should be matched.

It is understood that the present invention, being a modification of that which is disclosed in my now abandoned U.S. patent application Ser. No. 346,147, is capable of operating with all the modifications of the spectrophotometric apparatus disclosed in that patent application. Thus, the disclosure of the aforementioned patent application is incorporated herein by reference.

In a modification of the bridge sensor shown in FIG. 2, lamp light source 12 (shown in phantom lines) illuminating the specimen through aperture 17 in FIG. 1a is in series with the +12 volt battery power source. If the photosensor 22 resistance decreases with increasing light the bridge circuit will draw more current, and the increase in current will result in an increase of light output of the lamp, which will, in turn, increase the sensitivity of the photosensor. This condition will stabilize soon after the current has been switched on. This is therefore an alternative and improved modification of the bridge measuring system.

A significant feature of the invention is that the source of radiation for the specimen, such as a two or three watt incandescent lamp, is connected to the bridge circuit between the power source and the bridge circuit, and more specifically, in the circuit network formed by the first mentioned solid state device and the photosensitive device. The lowered impedance of that bridge circuit with a decrease in the resistance of the photosensitive device resulting from increasing light radiation from the radiation source, causes increased current through the radiation source such that the intensity of radiation therefrom is increased, thereby enhancing and increasing the radiation available for irradiating the specimen. This effect is aided by the amplification factor of the first mentioned solid state device.

Thus, in addition to the advantage obtained by a solid state actuated electronic bridge circuit, which provides increased measurement sensitivity, the invention affords commensurate enhancement of the radiation from the radiation source.

It is desired that the present invention not be limited to the embodiment specifically described above, but that it include all such modifications and variations that would be obvious to those skilled in the spectrophotometric or densitometer art to which the invention pertains. The scope of my invention should be determined by the equivalents of the various expressions recited in the following claims.

What is claimed is:

1. Apparatus for detecting spectrophotometric characteristics of a specimen, comprising;

a portable housing;

a light source for emitting radiation and mounted within said housing;

means for producing monochromatic light from said emitted radiation;

means for transmitting said monochromatic light to irradiate said specimen therewith; and photosensitive detector means responsive to the monochromatic light reflected from said specimen to provide output signals representative of the spectrophotometric characteristics of said specimen, and including light responsive means responsive to said reflected light and having an impedance characteristic variable in response thereto, a bridge circuit having a first arm including a first solid state device responsive to said variable impedance characteristic to generate a first amplified output, signal representative of said spectrophotometric characteristics, a second solid state device connected in a second arm of said bridge and responsive to said first amplified output signal to produce a second output signal representative thereof, means connected in a third arm of said bridge for calibrating said bridge and connected to said first solid state device, resistance means connected in the fourth arm of said bridge and connected to said second solid state device, whereby said second output signal represents the spectrophotometric characteristics of said specimen.

2. Apparatus as claimed in claim 1 further comprising a solid state buffer amplifier device responsive to said second output signal to provide an amplified output signal representative of the spectrophotometric characteristics of said specimen.

3. Apparatus as claimed in claim 2 wherein said first and second solid state devices are respective first and second transistors with said light response means connected in the emitter circuit of the first transistor, the base of said first transistor being connected to a voltage source, and the collector of said first transistor being connected to said calibrating means, the base, collector and emitter of said second transistor being respectively connected to the collector of said first transistor, said resistance means, and to ground through a second resistance means.

4. Apparatus as claimed in claim 3 wherein said buffer amplifier device is a third transistor having the base-emitter electrode thereof connected across the collector-emitter electrode of said second transistor.

5. Apparatus as claimed in any one of claims 1, 2, 3, or 4 further comprising indicating means connected to said first and second output signals to provide a visual indication of the spectrophotometric characteristics of the specimen.

6. Apparatus as claimed in any one of claims 1, 2, 3 or 4 and wherein said light source is connected to said bridge circuit such that the emitted radiation is increased with decreasing impedance of said variable impedance of said light responsive means and decreased with increasing impedance of said light responsive means.

7. Apparatus as claimed in any one of claims 1, 2, 3, or 4 wherein said means for producing monochromatic light includes a plurality of monochromatic filters each having respectively different transmittance characteristics over a different range of the light spectrum.

8. Apparatus as claimed in any one of claims 1, 2, 3 or 4 wherein said portable housing includes a first aperture for emitting light from said light source to the exterior of said housing and a second aperture for receiving light reflected from said specimen, and further comprising monochromatic filter means being mounted in confronting relationship to said second aperture, and said light responsive means being mounted within said housing to receive the light transmitted through said second aperture.

9. Apparatus as claimed in claim 8 further comprising means for calibrating said photosensitive detector means with a calibrating substance having known spectrophotometric characteristics and mounted to the exterior of said portable housing to receive light passing through said first aperture and to reflect light through said second aperture.

* * * * *